US006774129B2

(12) United States Patent
Kennis et al.

(10) Patent No.: US 6,774,129 B2
(45) Date of Patent: Aug. 10, 2004

(54) BENZOTHIENO[3,2-C]PYRIDINES AS α2 ANTAGONISTS

(75) Inventors: Ludo Edmond Josephine Kennis, Turnhout (BE); Serge Maria Aloysius Pieters, KK Hulst (BE); François Paul Bischoff, Vosselaar (BE)

(73) Assignee: Janssen Pharmaceutica N.V., Beerse (BE)

( * ) Notice: Subject to any disclaimer, the term of this patent is extended or adjusted under 35 U.S.C. 154(b) by 130 days.

(21) Appl. No.: 10/123,338

(22) Filed: Apr. 16, 2002

(65) Prior Publication Data

US 2002/0169178 A1 Nov. 14, 2002

Related U.S. Application Data

(62) Division of application No. 09/806,432, filed as application No. PCT/EP99/07418 on Oct. 1, 1999.

(30) Foreign Application Priority Data

Oct. 6, 1998 (EP) ............................................. 98203363

(51) Int. Cl.⁷ .................... C07D 495/04; A61K 31/435
(52) U.S. Cl. ...................... 514/258; 514/259; 514/291; 514/265; 514/267; 544/284; 544/278; 544/268; 544/250; 546/80
(58) Field of Search ............................ 544/284, 278, 544/268, 250; 514/259, 291, 258, 265, 267; 546/80

(56) References Cited

U.S. PATENT DOCUMENTS 3,752,820 A   8/1973   Suh .................... 260/294.8

FOREIGN PATENT DOCUMENTS

| EP | 0 178 201 | 4/1986 |
|---|---|---|
| EP | 0 214 556 | 3/1987 |
| EP | 0 339 959 | 11/1989 |
| WO | WO 98/45297 | 10/1998 |

OTHER PUBLICATIONS

Montgomery, et al., "Neurotransmitter system interactions revealed by drug–induced changes in motivated behavior", *Pharmacol. Biochem. Behav.*, 1999, 62, 643–657.

International Search Report Based on International Application No: PCT/EP99/07418 dated Jan. 13, 2000.

*Primary Examiner*—Mukund J. Shah
*Assistant Examiner*—Hong Liu
(74) *Attorney, Agent, or Firm*—Woodcock Washburn LLP

(57) ABSTRACT

The present invention concerns the compounds of formula (I)

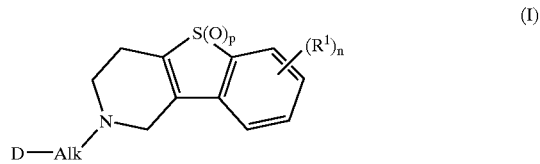

the N-oxides, the pharmaceutically acceptable addition salts and the stereochemically isomeric forms thereof, wherein each $R^1$ is independently hydrogen, halogen, $C_{1-6}$alkyl, nitro, hydroxy or $C_{1-4}$alkyloxy; Alk is $C_{1-6}$alkanediyl; n is 1 or 2; p is 0, 1 or 2; D is an optionally substituted mono-, bi- or tricyclic nitrogen containing heterocycle having central $α_2$-adrenoceptor antagonist activity. It further relates to their preparation, compositions comprising them and their use as a medicine.

12 Claims, No Drawings

BENZOTHIENO[3,2-C]PYRIDINES AS α2 ANTAGONISTS

CROSS REFERENCE TO RELATED APPLICATIONS

This application is a divisional application of 09/806,432 filed Mar. 30, 2001, which is a national stage application under 35 U.S.C. § 371 of PCT/EP99/07418, filed Oct. 1, 1999, which claims priority from EP 98.203.363.1, filed Oct. 6, 1998.

The present invention concerns benzothieno[3,2-c] pyridine derivatives having central $\alpha_2$-adrenoceptor antagonist activity. It further relates to their preparation, compositions comprising them and their use as a medicine.

Central $\alpha_2$-adrenoceptor antagonists are known to increase noradrenaline release by blocking presynaptic $\alpha_2$-receptors which exert an inhibiting control over the release of the neurotransmitter. By increasing the noradrenaline concentrations, $\alpha_2$-antagonists can be used clinically for the treatment or prophylaxis of depression, cognitive disturbances, Parkinson's disease, diabetes mellitus, sexual dysfunction and impotence, elevated intraocular pressure, and diseases related to disturbed enterokinesia, since all these conditions are associated with a deficiency of noradrenaline in the central or peripheral nervous system.

The compounds of the present invention are novel and have a specific and selective binding affinity for the different known subtypes of the $\alpha_2$-adrenoceptors, i.e. the $\alpha_{2A}$, $\alpha_{2B}$ and $\alpha_{2C}$-adrenoceptor.

The present invention concerns the compounds of formula

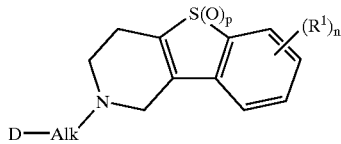

(I)

the N-oxide forms, the pharmaceutically acceptable addition salts and the stereochemically isomeric forms thereof, wherein:

each $R^1$ is independently hydrogen, halogen, $C_{1-6}$alkyl, nitro, hydroxy or $C_{1-4}$alkyloxy;

Alk is $C_{1-4}$alkanediyl;

n is 1 or 2;

p is 0, 1 or 2;

D is 1- or 2-benzimidazolyl, 2(3H)benzoxazolone-3-yl or a radical of formula

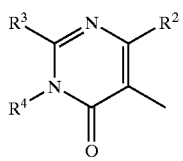 (a)

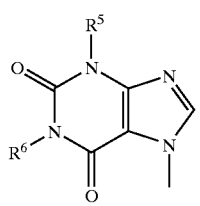 (b)

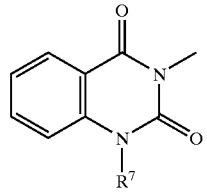 (c)

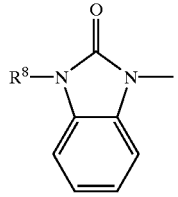 (d)

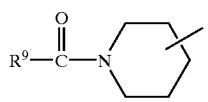 (e)

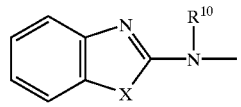 (f)

 (g)

wherein
each X independently represents O, S or $NR^{12}$;
$R^2$ is hydrogen, $C_{1-6}$alkyl, aryl or aryl$C_{1-6}$alkyl;
$R^3$ is hydrogen, $C_{1-6}$alkyl, $C_{1-6}$alkyloxy, $C_{1-6}$alkylthio, amino or mono- or di($C_{1-6}$alkyl)amino;
$R^4$, $R^5$, $R^6$, $R^7$, $R^8$, $R^{10}$, $R^{11}$ and $R^{12}$ each independently are hydrogen or $C_{1-6}$alkyl;
$R^9$ is hydrogen, $C_{1-6}$alkyl or aryl; or
$R^3$ and $R^4$ taken together may form a bivalent radical —$R^3$—$R^4$— of formula

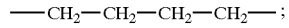 (a-1)

 (a-2)

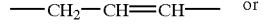 (a-3)

 (a-4) or

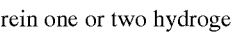 (a-5)

wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alkylidene or aryl$C_{1-6}$alkylidene; or

 (a-6)

```
——S—CH₂—CH₂—CH₂—;         (a-7)
——S—CH=CH—;               (a-8)
——NH—CH₂—CH₂—;            (a-9)
——NH—CH₂—CH₂—CH₂—;        (a-10)
——NH—CH=CH—;              (a-11)
——NH—CH=N—;               (a-12)
——S—CH=N—  or             (a-13)
——CH=CH—O—;               (a-14)
``` wherein one or where possible two or three hydrogen atoms in said radicals (a-6) to (a-14) each independently may be replaced by $C_{1-6}$alkyl or aryl; and aryl is phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

As used in the foregoing definitions the term halogen is generic to fluoro, chloro, bromo and iodo. The term $C_{1-6}$alkyl defines straight and branched saturated hydrocarbons, having from 1 to 6 carbon atoms such as, for example, methyl, ethyl, propyl, butyl, 1-methylethyl, 1,1-dimethylethyl, 2-methylpropyl, pentyl, hexyl and the like. The term $C_{1-10}$alkyl is meant to include $C_{1-6}$alkyl radicals and the higher homologues thereof having 7 to 10 carbon atoms such as, for example, heptyl, octyl, nonyl, decyl and the like. The term $C_{1-6}$alkanediyl defines bivalent straight or branch chained alkanediyl radicals having from 1 to 6 carbon atoms such as, for example, methylene, 1,2-ethanediyl, 1,3-propanediyl, 1,4-butanediyl, 1,5-pentanediyl, 1,6-hexanediyl and the like; the term $C_{1-6}$alkylidene defines bivalent straight or branch chained alkylidene radicals having from 1 to 6 carbon atoms such as, for example, methylene, ethylidene, 1-propylidene, 1-butylidene, 1-pentylidene, 1-hexylidene and the like.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the N-oxide forms, the pharmaceutically acceptable addition salts and all stereoisomeric forms.

Suitably, aryl is phenyl or phenyl substituted halo or $C_{1-6}$alkyl.

A special group of compounds are those compounds of formula (I) wherein p is 0.

An interesting group of compounds are those compounds of formula (I) wherein n is 1 and $R^1$ is hydrogen, chloro, fluoro, methyl, methoxy or nitro, in particular $R^1$ is hydrogen or chloro; or, wherein n is 2 and both $R^1$ are methoxy. Preferred positions for $R^1$ are position 7 and 8 as depicted below.

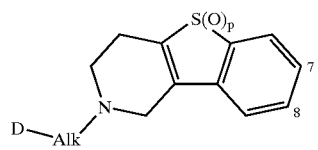

Another interesting group of compounds are those compounds of formula (I) wherein Alk is methylene, 1,2-ethanediyl, 1,3-propanediyl, 1,4-butanediyl or 1,5-pentanediyl, in particular 1,2-ethanediyl, 1,3-propanediyl, 1,4-butanediyl, more in particular 1,2-ethanediyl.

Still another interesting group of compounds are those compounds of formula (I) wherein D is a radical of formula (a), (b), (c), (d) or (f).

Particular compounds are those compounds of formula (I) wherein D is a radical of formula (a) wherein $R^2$ is $C_{1-6}$alkyl, aryl or aryl$C_{1-6}$alkyl, and $R^3$ and $R^4$ form a bivalent radical of formula —$R^3$—$R^4$—, and suitably —$R^3$—$R^4$— is a radical of formula (a-5) or (a-8); or D is a radical of formula (b) wherein R5 and R6 are $C_{1-6}$alkyl; or D is a radical of formula (c) wherein $R^7$ is hydrogen; or D is a radical of formula (d) wherein $R^8$ is hydrogen; or D is a radical of formula (f) wherein $R^{10}$ is hydrogen and X is O or S, in particular S.

Preferred compounds are those compounds of formula (I) wherein n is 1 and $R^1$ is hydrogen or chloro, p is 0, Alk is 1,2-ethanediyl and D is a radical of formula (a), (b), (c), (d) or (f).

Most preferred compounds are the compounds depicted below or their N-oxide forms, the pharmaceutically acceptable addition salts and the stereochemically isomeric forms thereof:

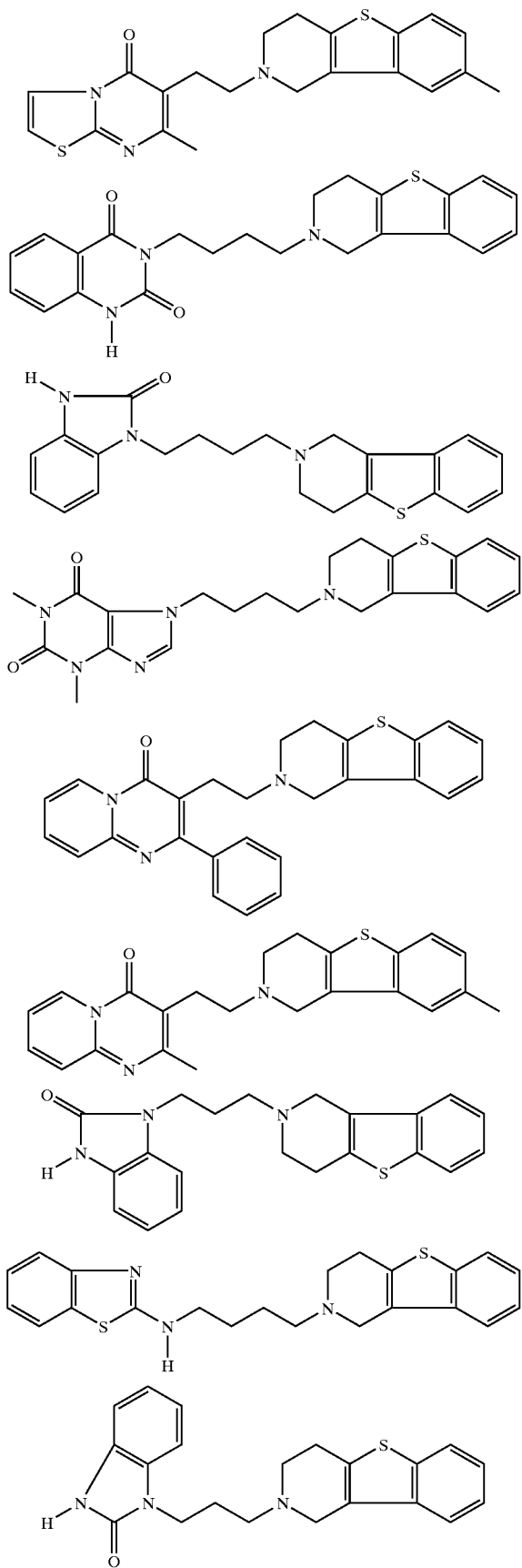

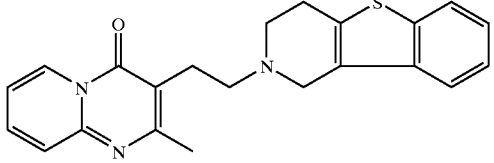

The compounds of formula (I) can generally be prepared by N-alkylating a benzo-thieno[3,2-c]pyridine derivative of formula (II) with an alkylating reagent of formula (III) following the procedure described in EP-A-0,037,265, EP-A-0,070,053, EP-A-0,196,132 and in EP-A-0,378,255. Conveniently, both intermediates are reacted in a suitable solvent such as, for example, methylisobutyl keton, in the presence of a base such as, for example, sodium carbonate, and optionally in the presence of a catalyst such as, for example, potassium iodide.

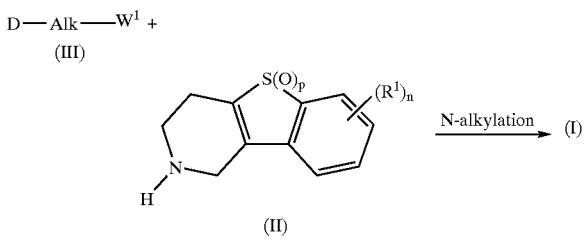

In intermediate (III), $W^1$ represents an appropriate reactive leaving group such as, for example, halo, e.g. chloro, bromo or iodo; sulfonyloxy, e.g. methanesulfonyloxy, 4-methylbenzenesulfonyloxy.

In this and the following reactions, the reaction products may be isolated from the reaction medium and, if necessary, further purified according to methodologies generally known in the art such as extraction, crystallization, trituration and chromatography.

The compounds of formula (I) wherein D is a radical of formula (e), being represented by formula (I–e), may be prepared by deprotecting a N-protected intermediate of formula (IV) wherein P is a protective group such as, for example, a $C_{1-4}$alkyloxy-carbonyl group, and subsequently N-acylating the resulting intermediate with an acyl derivative of formula (V) wherein $W^2$ is an appropriate reactive leaving group such as, for example, a halogen. The reaction may be performed in a suitable solvent such as, for example, chloroform, methylisobutyl keton or an alcohol, in the presence of a base such as, for example, sodium carbonate.

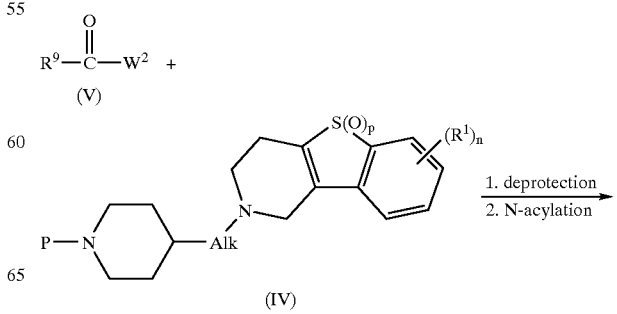

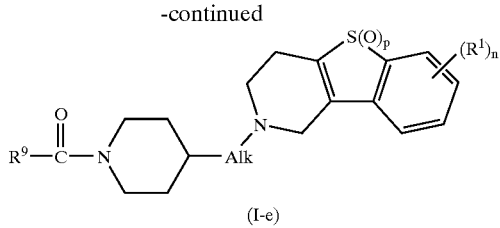

The compounds of formula (I) wherein D is a radical of formula (f), being represented by formula (I-f), can be prepared by N-alkylating an amine of formula (VI) with an intermediate of formula (VII) wherein $W^3$ is an appropriate reactive leaving group such as, for example, a halogen.

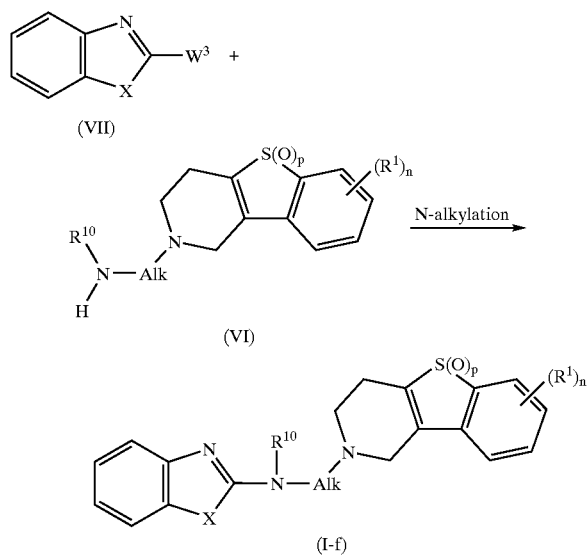

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (II) wherein X is S can be prepared analogous to the procedure described in Capps et al. (J. Am. Chem. Soc., 1953, p. 697) or U.S. Pat. No. 3,752,820.

A particular synthesis route for the preparation of intermediates of formula (II) is depicted in scheme 1.

Scheme 1

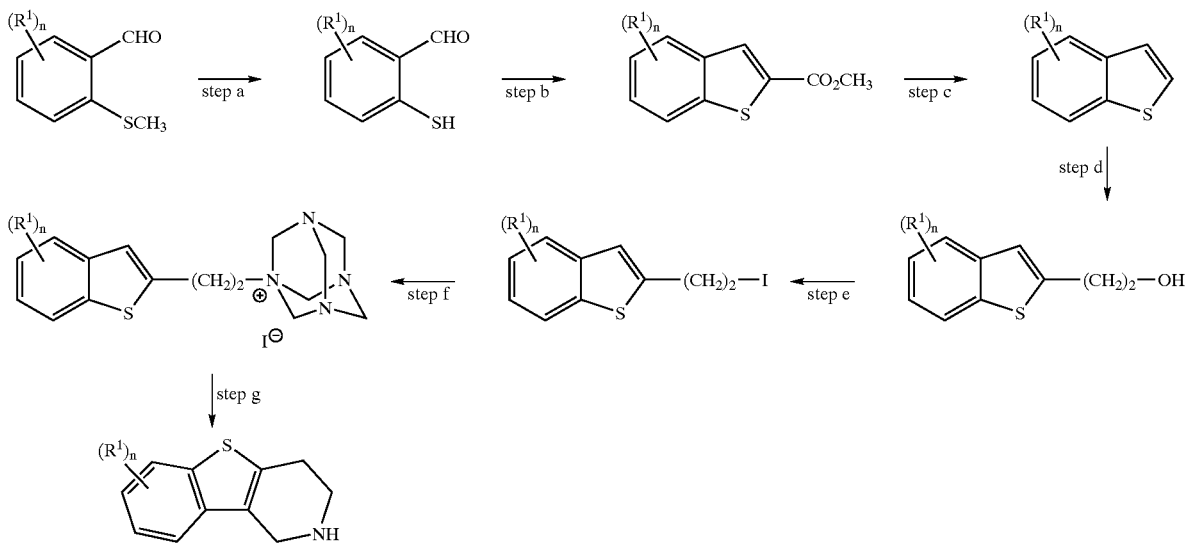

Step a can be performed analogous to the procedure described in Tetrahedron (1981), 37, p 979–982. Benzofurans resulting from step c have been used as intermediates in U.S. Pat. No. 4,210,655. The further reaction steps are analogous to the reaction procedures described in U.S. Pat. No. 3,752,820.

Alternatively, intermediates of formula (II) can be prepared using the reaction steps depicted in scheme 2.

Scheme 2

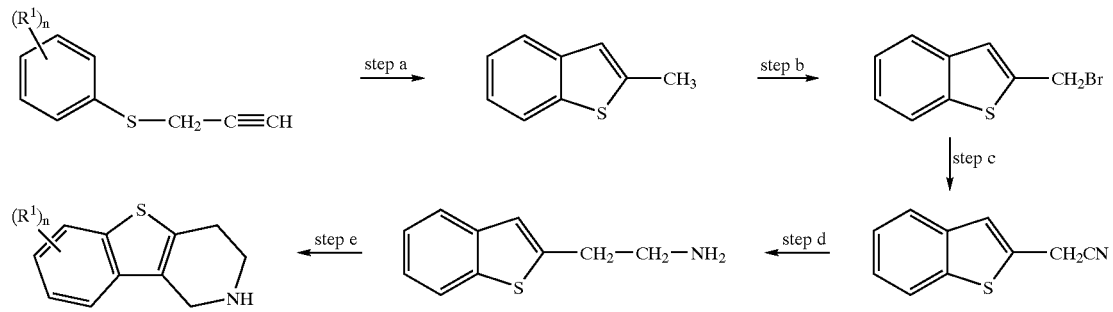

Step a can be performed analogous to the procedure described in Heterocycles (1994), 39(1), p. 371–380. Step b can be performed analogous to the procedure described in J. Med. Chem. (1986), 29(9), p. 1643–1650. Further reaction steps can be performed analogous to the ones described in J. Heterocycl. Chem. (1979), 16, p. 1321.

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the N-oxides, the pharmaceutically acceptable addition salts and stereochemically isomeric forms thereof, block the presynaptic $\alpha_2$-receptors on central noradrenergic neurons thus increasing the noradrenaline release. Blocking said receptors will suppress or relieve a variety of symptoms associated with a deficiency of noradrenaline in the central or peripheral nervous system.

Therapeutic indications for using the present compounds are depression, cognitive disturbances, Parkinson's disease, diabetes mellitus, sexual dysfunction and impotence and elevated intraocular pressure.

Blocking $\alpha_2$ receptors in the central nervous system has also been shown to enhance the release of serotonine which may add to the therapeutic action in depression (Maura et al., 1992, Naunyn-Schmiedeberg's Arch. Pharmacol., 345 : 410–416).

It has also been shown that blocking $\alpha_2$ receptors may induce an increase of extracellular DOPAC (3,4-dihydrophenylacetic acid) which is a metabolite of dopamine and noradrenaline.

In view of the usefulness of the subject compounds in the treatment of diseases associated with a deficiency of noradrenaline in the central nervous system, in particular depression and Parkinson's disease, the present invention provides a method of treating warm-blooded animals suffering from such diseases, in particular depression and Parkinson's disease, said method comprising the systemic administration of an therapeutically effective amount of a compound of formula (I) or a pharmaceutically acceptable addition salt thereof.

The present compounds are also potentially useful in the treatment of Alzheimer's disease and dementia as it is known that $\alpha_2$-antagonists promote the release of acetylcholine (Tellez et al. 1997, J. Neurochem. 68:778–785).

In general it is contemplated that an effective therapeutic daily amount would be from about 0.01 mg/kg to about 4 mg/kg body weight.

The present invention thus also relates to compounds of formula (I) as defined hereinabove for use as a medicine. Further, the present invention also relates to the use of a compound of formula (I) for the manufacture of a medicament for treating depression or Parkinson's disease.

Ex vivo as well as in vitro receptor signal-transduction and receptor binding studies can be used to evaluate the $\alpha_2$ adrenoceptor antagonism of the present compounds. As indices of central $\alpha_2$-adrenoceptor blockade in vivo, the reversal of the loss of righting reflex observed in rats after intravenous injection of xylazine and inhibition of the tremors induced by reserpine in rats can be used.

The compounds of the present invention also have the ability to rapidly penetrate into the central nervous system.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

Experimental Part

Preparation of the Intermediate Compounds

EXAMPLE A1 a) A mixture of 1,2,3,4-tetrahydro[1]benzothieno[3,2-c]pyridine HCl (1:1) (0.02 mol), 1,1-dimethylethyl (4chlorobutyl)carbamate (0.044 mol), $Na_2CO_3$ (0.05 mol) and KI (catalytic quantity) in 4-methyl-2-pentanone (200 ml) was stirred and refluxed overnight, then cooled to room temperature and the solvent was evaporated. The residue was washed with water and extracted with $CH_2Cl_2$. The separated organic layer was dried, filtered and the solvent evaporated. The residue was purified by column chromatography over silica gel (eluent: $CH_2Cl_2/CH_3OH$ 90/10). The desired fractions were collected and the solvent was evaporated, yielding 1,1-dimethylethyl [4-(3,4-dihydro[1]benzothieno[3,2-c]pyridine-2(1H)-yl)butyl]carbamate (interim.1).

b) A mixture of intermediate (1) (0.02 mol) in HCl/2-propanol (20 ml) and 2-propanol (150 ml) was stirred and refluxed for 30 min, then cooled to room temperature. The precipitate was filtered off and dried, yielding 4.9 g of 3,4-dihydro[1]benzothieno-[3,2-c]pyridine-2(1H)-butanamine dihydrochloride (73%) (intern. 2).

EXAMPLE A2 a) Butyllithium (2.5 M) (0.27 mol) was added dropwise to 6-methoxybenzo[b]-thiophene (0.25 mol) in tetrahydrofuran (1000 ml), stirred at −30° C. The mixture was stirred for 10 min at −30° C. Ethylene oxide (0.38 mol in 100 ml tetrahydrofuran) was added dropwise at −30° C. The mixture was allowed to warm to room temperature and stirred for 3 hours. The mixture was acidified with dilute HCl solution. The solvent was evaporated. The residue was diluted with water and this mixture was extracted with $CH_2Cl_2$. The separated organic layer was dried, filtered and the solvent evaporated. The residue was stirred in hexane, filtered off and dried, yielding 41.3 g of 6-methoxybenzo[b]thiophene-2-ethanol (interm. 3).

b) Methanesulfonyl chloride (0.21 mol) was added to a mixture of intermediate (3) (0.19 mol) and N,N-diethylethanamine (0.21 mol) in $CH_2Cl_2$ (1 L), stirred at 0° C. The reaction mixture was stirred for 4 hours at room temperature, then poured out into water. The separated organic layer was dried, filtered and the solvent evaporated. The residue was triturated under diisopropyl ether, filtered off and dried, yielding 50.5 g of 6-methoxybenzo[b]thiophene-2-ethanol methanesulfonate (ester) (interm.4).

c) A mixture of intermediate (4) (0.18 mol) and sodiumiodide (0.45 mol) in 2-propanone (1000 ml) was stirred and refluxed for 9 hours, then cooled to room temperature and the solvent was evaporated. The residue was washed with water and extracted with $CH_2Cl_2$. The separated organic layer was dried, filtered and the solvent evaporated, yielding 57 g of 2-(2-iodoethyl)-6-methoxybenzo[b]thiophene (interm.5).

d) Intermediate (5) (0.18 mol) was added portionwise to a mixture of 1,3,5,7-tetra-azatricyclo[3.3.1.13,7]decane (0.45 mol) in $CHCl_3$ (600 ml). The reaction mixture was stirred and refluxed overnight, then cooled to room temperature. The precipitate was filtered off and dried, yielding 54.2 g of 1-[2-(6-methoxybenzo[b]thiophen-2-yl)ethyl]-1,3,5,7-tetraazatricyclo[5.1.1.1-5,7]decanium iodide (interm.6).

e) A mixture of intermediate (6) (0.12 mol) and HCl(0.50 mol) in ethanol (171 ml) was stirred for 2 days at room temperature. More HCl (10 ml) and ethanol (40 ml) were added and the reaction mixture was stirred and refluxed for one hour, then cooled to room temperature. The solvent was evaporated. The residue was stirred in 2-propanol, then filtered off. The solid was dried and reconverted into the free base with 20% NaOH. The separated organic layer was dried, filtered and the solvent evaporated. The residue was dissolved in 2-propanol and converted into the hydrochloric acid salt (1:1) with HCl/2-propanol. The precipitate was filtered off and dried, yielding 13.1 g of 1,2,3,4-tetrahydro-7-methoxy[1]benzothieno[3,2-c]pyridine (50%) (interm.7).

In an analogous way were also prepared:

1,2,3,4-tetrahydro-8-methyl-[1]benzothieno[3,2-c]pyridine hydrochloride(1:1) (interm.8); and 1,2,3,4-tetrahydro-8-fluoro-[1]benzothieno[3,2-c]pyridine hydrochloride(1:1) (interm.9).

Preparation of the Compounds of Formula (I)

EXAMPLE B1

A mixture of 1,2,3,4-tetrahydro-benzothieno[3,2-c]pyridine [prepared analogous to the procedure described in J. Am. Chem. Soc., 1953, p. 697] (0.009 mol), 3-(2-chloroethyl)-2-methyl-4H-pyrido[1,2-a]pyrimidin-4-one (0.011 mol), $Na_2CO_3$ (0.023 mol) and KI (catalytic quantity) in methylisobutyl keton (100 ml) was stirred and refluxed overnight, then cooled to room temperature and the solvent was evaporated. The residue was washed with water and extracted with $CH_2Cl_2$. The separated organic layer was dried, filtered and the solvent evaporated. The residue was purified by column chromatography over silica gel (eluent: $CH_2Cl_2/CH_3OH$ 90/10). The desired fractions were collected and the solvent was evaporated. The residue was converted into the (E)-2-butenedioic acid salt (2:1). The precipitate was filtered off and dried, yielding 2.3 g (47%) of 3-[2-(3,4-dihydro-[1]benzothieno[3,2-c]pyridin-2(1H)-yl) ethyl]4H-pyrido[1,2-a]pyrimidin-4-one (E)-2-butenedioate (2:1) (comp. 1).

EXAMPLE B2

$Na_2CO_3$ (0.100 g) was added to a solution of 1,2,3,4-tetrahydro-benzothieno[3,2-c]-pyridine (0.00044 mol) and 3-(4-chlorobutyl)-2,4(1H,3H)quinazolinedione (0.100 g) in methylisobutyl keton (2 ml) and the resulting reaction mixture was stirred overnight at 100° C. The desired compound was isolated and purified by HPLC over Kromasil Spherical underivated silica gel (eluent: $CH_2Cl_2/(CH_2Cl_2/CH_3OH$ 90/10)/$CH_3OH$ (0 min) 100/0/0, (10.50 min) 0/100/0, (12.50 min) 50/0/50, (14.00 min) 0/0/100, (15.01–20.00 min) 100/0/0). The pure fractions were collected and the solvent was evaporated, yielding 0.025 g of 3-[4-(3,4-dihydro-[1]benzothieno[3,2-c]pyridin-2(1H)-yl) butyl]-1,3-quinazoline-2,4(1H,3H)-dione (comp. 6).

EXAMPLE B3

A mixture of intermediate (2) (0.01 mol), 2-chlorobenzothiazole (0.012 mol) and $Na_2CO_3$ (0.015 mol) in 2 ethoxy ethanol (50 ml) was stirred and refluxed overnight. The reaction mixture was filtered hot and the filtrate was allowed to cool to room temperature. The solvent was evaporated. The residue was purified by column chromatography over silica gel (eluent: $CH_2Cl_2/CH_3OH$ 90/10). The desired fractions were collected and the solvent was evaporated. The residue was converted into the hydrochloric acid salt (1:2). The precipitate was filtered off and dried, yielding 2.3 g of N-2-benzothiazolyl-3,4-dihydro[1]benzothieno[3,2-c]pyridine-2(1H)-butanamine dihydrochloride (49%) (comp. 18).

Table 1 lists compounds of formula (I) which were made analogous to one of the above examples.

| Co. No. | Ex. No. | $R^1$ | Alk | D | Salt form |
|---|---|---|---|---|---|
| 1 | B1 | H | —$(CH_2)_2$— | pyrido[1,2-a]pyrimidin-4-one-3-yl (2-methyl) | (E)-2-butenedioate (2:1) |
| 2 | B1 | H | —$(CH_2)_2$— | thiazolo-pyrimidinone-yl (methyl) | (E)-2-butenedioate (2:1) |
| 3 | B1 | H | —$(CH_2)_3$— | benzimidazol-2(3H)-one-1-yl | (E)-2-butenedioate (2:1) |

-continued

[Structure: tricyclic thieno-fused system with numbered positions 1-8, N-2 bearing D—Alk substituent, R¹ on aromatic ring]

| Co. No. | Ex. No. | R¹ | Alk | D | Salt form |
|---|---|---|---|---|---|
| 4 | B2 | H | —(CH₂)₃— | benzimidazol-2(3H)-one-1-yl | — |
| 5 | B2 | H | —(CH₂)₄— | benzimidazol-2(3H)-one-1-yl | — |
| 6 | B2 | H | —(CH₂)₄— | quinazoline-2,4(1H,3H)-dione-3-yl | — |
| 7 | B1 | 8-Cl | —(CH₂)₂— | 2-methyl-4-oxo-4H-pyrido[1,2-a]pyrimidin-3-yl | — |
| 8 | B1 | 8-Cl | —(CH₂)₂— | 6-methyl-7-oxo-7H-thiazolo[3,2-a]pyrimidin-5-yl | (E)-2-butenedioate (2:1) |
| 9 | B1 | H | —(CH₂)₃— | quinazoline-2,4(1H,3H)-dione-3-yl | — |
| 10 | B1 | 8-CH₃ | —(CH₂)₂— | 2-methyl-4-oxo-4H-pyrido[1,2-a]pyrimidin-3-yl | HCl (1:2), H₂O (1:1) |
| 11 | B1 | 8-CH₃ | —(CH₂)₂— | 6-methyl-7-oxo-7H-thiazolo[3,2-a]pyrimidin-5-yl | (E)-2-butenedioate (1:1) |

-continued

| Co. No. | Ex. No. | R¹ | Alk | D | Salt form |
|---|---|---|---|---|---|
| 12 | B1 | 8-Cl | —(CH$_2$)$_3$— | 1,3-dihydro-2H-benzimidazol-2-one (N-linked) | (E)-2-butenedioate (2:1) |
| 13 | B1 | 8-F | —(CH$_2$)$_2$— | 2-methyl-4H-thiazolo[3,2-a]pyrimidin-4-one-3-yl | — |
| 14 | B1 | 8-F | —(CH$_2$)$_2$— | 2-methyl-4H-pyrido[1,2-a]pyrimidin-4-one-3-yl | — |
| 15 | B1 | 8-F | —(CH$_2$)$_3$— | 1,3-dihydro-2H-benzimidazol-2-one (N-linked) | (E)-2-butenedioate (2:1) |
| 16 | B2 | H | —(CH$_2$)$_4$— | 1,3-dimethylxanthin-7-yl | (E)-2-butenedioate (1:1) |
| 17 | B2 | H | —(CH$_2$)$_2$— | 1,3-dihydro-2H-benzimidazol-2-one (N-linked) | HCl (1:1) |
| 18 | B3 | H | —(CH$_2$)$_4$— | benzothiazol-2-ylamino | HCl (1:2) |
| 19 | B1 | H | —(CH$_2$)$_2$— | 2-phenyl-4H-pyrido[1,2-a]pyrimidin-4-one-3-yl | HCl (1:2) |

-continued

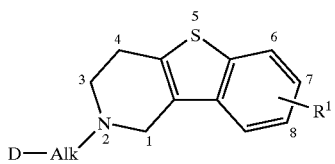

| Co. No. | Ex. No. | R¹ | Alk | D | Salt form |
|---|---|---|---|---|---|
| 20 | B1 | H | —(CH₂)₂— | (pyrido-pyrimidinone with benzyl) | (E)-2-butenedioate (1:1) |
| 21 | B1 | 7-OCH₃ | —(CH₂)₂— | (pyrido-pyrimidinone with CH₃) | HCl (1:1); H₂O (1:1); (E)-2-butenedioate (2:1) |
| 22 | B1 | 7-OCH₃ | —(CH₂)₂— | (thiazolo-pyrimidinone with CH₃) | (E)-2-butenedioate (2:3), H₂O (1:1) |
| 23 | B1 | 7-OCH₃ | —(CH₂)₃— | (benzimidazolone) | (E)-2-butenedioate (2:3) |
| 24 | B1 | 7-Cl | —(CH₂)₂— | (pyrido-pyrimidinone with CH₃) | HCl (1:2), H₂O (1:1), 2-propanolate (1:1) |

C. Pharmacological Examples

EXAMPLE C.1

In vitro Binding Affinity for $\alpha_2$ Receptors

The interaction of the compounds of formula (I) with $\alpha_2$ receptors was assessed in in vitro radioligand binding experiments.

In general, a low concentration of a radioligand with a high binding affinity for a particular receptor is incubated with a sample of a tissue preparation enriched in a particular receptor or with a preparation of cells expressing cloned human receptors in a buffered medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Various concentrations of the test compound are added to the incubation mixture containing the receptor preparation and the radioligand. Binding of the radioligand will be inhibited by the test compound in proportion to its binding affinity and its concentration.

The radioligand used for $\alpha_{2A}$, $\alpha_{2B}$ and $\alpha_{2C}$ receptor binding is ³H-rauwolscine and the receptor preparation used is the Chinese Hamster Ovary (CHO) cell expressing cloned human $\alpha_{2A}$, $\alpha_{2B}$ and $\alpha_{2C}$ receptors.

The compounds exemplified in the experimental part above all had an $IC_{50}$ value (concentration whereby 50% of the receptors is inhibited) for each of the three receptors of at least $10^{-6}$ M.

D. Composition Examples

"Active ingredient" (A.I.) as used throughout these examples relates to a compound of formula (I), a pharmaceutically acceptable addition salt or a stereochemically isomeric form thereof.

EXAMPLE D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.2

Film-Coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

EXAMPLE D.3

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound of formula

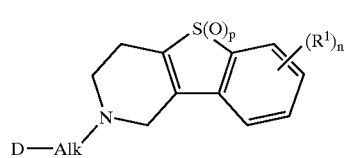

an N-oxide form, a pharmaceutically acceptable addition salt or a stereochemically isomeric form thereof, wherein:

each $R^1$ is independently hydrogen, halogen, $C_{1-6}$alkyl, nitro, hydroxy or $C_{1-4}$alkyloxy;

Alk is $C_{1-6}$alkanediyl;

n is 1 or 2;

p is 0, 1 or 2;

D is 1- or 2-benzimidazolyl, 2(3H)benzoxazolone-3-yl or a radical of formula

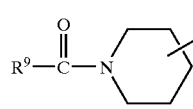

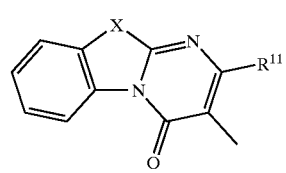

wherein each X independently represents O, S or $NR^{12}$;

$R^2$ is hydrogen, $C_{1-6}$alkyl, aryl or aryl$C_{1-6}$alkyl;

$R^3$ is hydrogen, $C_{1-6}$alkyl, $C_{1-6}$alkyloxy, $C_{1-6}$alkylthio, amino or mono- or di($C_{1-6}$alkyl)amino;

$R^4$, $R^5$, $R^6$, $R^7$, $R^8$, $R^{10}$, $R^{11}$ and $R^{12}$ each independently are hydrogen or $C_{1-6}$alkyl;

$R^9$ is hydrogen, $C_{1-6}$alkyl or aryl; or $R^3$ and $R^4$ taken together may form a bivalent radical —$R^3$—$R^4$— of formula

 (a-1)

 (a-2)

 (a-3)

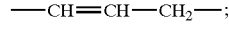 ; or (a-4)

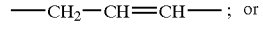 ; (a-5)

wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alkylidene or aryl$C_{1-6}$alkylidene; or
—$R^3$—$R^4$— may also be —S—$CH_2$—$CH_2$—; (a-6)

—S—$CH_2$—$CH_2$—$CH_2$—; (a-7)

—S—CH=CH—; (a-8)

—NH—$CH_2$—$CH_2$—; (a-9)

—NH—$CH_2$—$CH_2$—$CH_2$—; (a-10)

—NH—CH=CH—; (a-11)

—NH—CH=N—; (a-12)

—S—CH=N—; or (a-13)

—CH=CH—O—; (a-14)

wherein one or where possible two or three hydrogen atoms in said radicals (a-6) to (a-14) each independently may be replaced by $C_{1-6}$alkyl or aryl; and aryl is phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

2. A compound according to claim 1 wherein aryl is phenyl or phenyl substituted with halo or $C_{1-6}$alkyl.

3. A compound according to claim 2 wherein Alk is 1,2-ethanediyl, 1,3-propanediyl or 1,4-butanediyl.

4. A compound according to any one of claim 1 wherein n is 1 and $R^1$ is hydrogen, chloro, fluoro, methyl, methoxy or nitro.

5. A composition comprising a pharmaceutically acceptable carrier and, as active ingredient, a therapeutically effective amount of a compound of claim 1.

6. A process for preparing a composition, comprising the step of:
combining the compound of claim 1 as the active ingredient with a pharmaceutically acceptable carrier.

7. A process for preparing a compound according to claim 1, comprising the step of:
a) N-alkylating a benzothieno[3,2-c]pyridine derivative of formula (II) with an alkylating reagent of formula (III), D—Alk—$W^1$ +
(III)

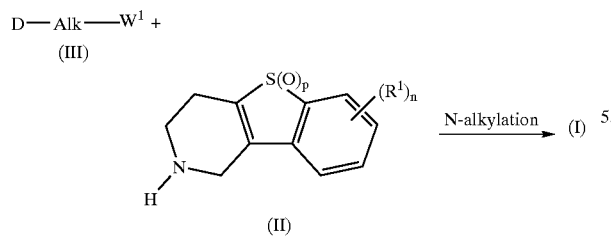

wherein $W^1$ represents an appropriate reactive leaving group, D, Alk, p, n and $R^1$ are as defined in claim 1, in a suitable solvent, in the presence of a base and optionally in the presence of a catalyst;

b) deprotecting a N-protected intermediate of formula (IV) wherein P is a protective group and Alk, p, n and $R^1$ are as defined in claim 1, and subsequently N-acylating the resulting intermediate with an acyl derivative of formula (V) wherein $W^2$ is an appropriate reactive leaving group and $R^9$ is as defined in claim 1, in a suitable solvent and in the presence of a base; thus forming a compound of formula (I-e); and

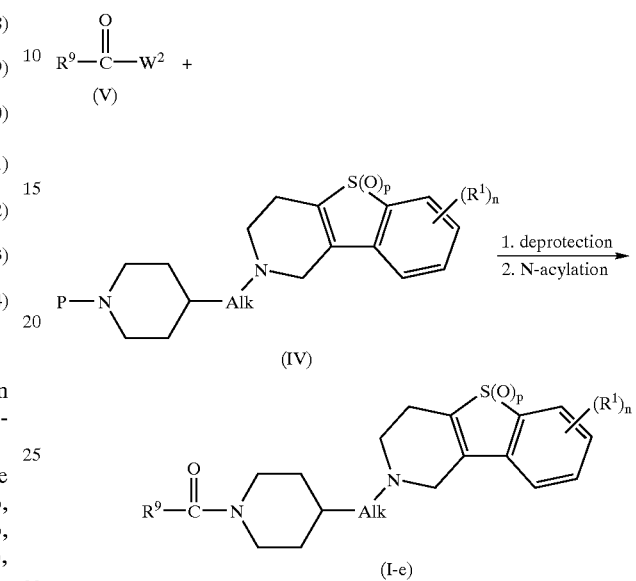

c) N-alkylating an amine of formula (VI) with an intermediate of formula (VII) wherein $W^3$ is an appropriate reactive leaving group;

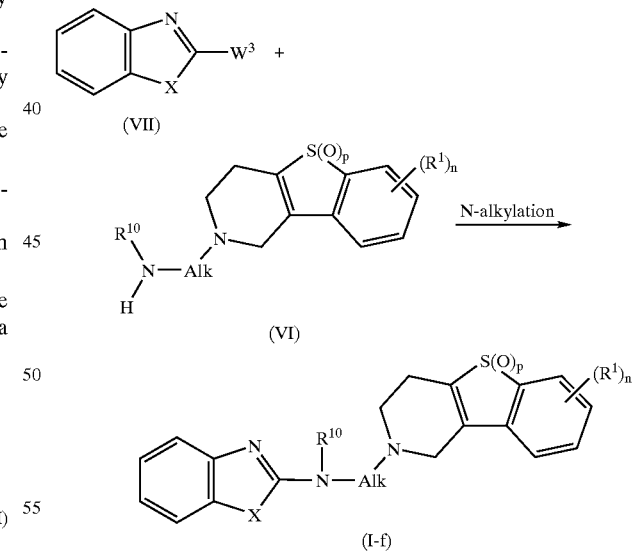

8. The process of claim 7, further comprising the step of converting compound of formula (I), stereochemically isomeric forms, or N-oxide forms thereof, into a therapeutically active non-toxic acid addition salt by treatment with an acid.

9. The process of claim 7, further comprising the step of converting compound of formula (I), stereochemically isomeric forms, or N-oxide forms thereof, into a therapeutically active non-toxic base addition salt by treatment with alkali.

10. The process of claim 7, further comprising the step of converting the acid addition salt form of compound of formula (I), stereochemically isomeric forms or N-oxide forms thereof, into the free base by treatment with alkali.

11. The process of claim 7, further comprising the step of converting the base addition salt form of compound of formula (I), stereochemically isomeric forms, or N-oxide forms thereof, into the free acid by treatment with acid.

12. A method of treating a disorder selected from the group consisting of depression and Parkinson's disease in a warm-blooded animal, comprising the step of:

administering to said warm-blooded animal a therapeutically effective amount of the compound of claim 1.

* * * * *

UNITED STATES PATENT AND TRADEMARK OFFICE
CERTIFICATE OF CORRECTION

PATENT NO. : 6,774,129 B2
DATED : August 10, 2004
INVENTOR(S) : Kennis et al.

It is certified that error appears in the above-identified patent and that said Letters Patent is hereby corrected as shown below:

Column 2,
Line 64, please add -- -$R^3$-$R^4$- may also be --.

Column 3,
Line 19, begin a new paragraph after "or aryl; and".

Column 23,
Line 35, delete "any one of".

Signed and Sealed this

Fifth Day of April, 2005

JON W. DUDAS
*Director of the United States Patent and Trademark Office*